(12) United States Patent
Sverdrup et al.

(10) Patent No.: US 9,814,728 B2
(45) Date of Patent: Nov. 14, 2017

(54) INHIBITION OF DUX4 EXPRESSION USING BROMODOMAIN AND EXTRA-TERMINAL DOMAIN PROTEIN INHIBITORS (BETI)

(71) Applicant: Saint Louis University, St. Louis, MO (US)

(72) Inventors: Francis M. Sverdrup, Lake Saint Louis, MO (US); Stephen J. Tapscott, Seattle, WA (US)

(73) Assignee: Saint Louis University, St. Louis, MO (US)

( * ) Notice: Subject to any disclaimer, the term of this patent is extended or adjusted under 35 U.S.C. 154(b) by 0 days.

(21) Appl. No.: 14/491,599

(22) Filed: Sep. 19, 2014

(65) Prior Publication Data

US 2015/0087636 A1    Mar. 26, 2015

Related U.S. Application Data

(60) Provisional application No. 61/880,565, filed on Sep. 20, 2013.

(51) Int. Cl.

| | |
|---|---|
| *A01N 43/00* | (2006.01) |
| *A61K 31/397* | (2006.01) |
| *A61K 31/551* | (2006.01) |
| *A61K 31/517* | (2006.01) |
| *A61K 31/4745* | (2006.01) |

(52) U.S. Cl.
CPC ........ *A61K 31/551* (2013.01); *A61K 31/4745* (2013.01); *A61K 31/517* (2013.01)

(58) Field of Classification Search
USPC .................................................. 514/210.01
See application file for complete search history.

(56) References Cited

PUBLICATIONS

Proserpio et al. (The Methyltransferase Smyd3 Mediates the Recruitment of Transcriptional Cofactors at the Myostatin and C-met Genes and Regulates Skeletal Muscle Atrophy. Genes & Development, (Jun. 1, 2013) vol. 27, No. 11, pp. 1299-1312).*
Lemmers et al. ("A Unifying Genetic Model for Facioscapulohumeral Muscular Dystrophy." Science 329.5999 (2010): 1650-1653).*
Tawil, Rabi, Facioscapulohumeral Muscular Dystrophy, Neurotherapeutics: The Journal of the American Society for Experimental NeuroTherapeutics, Oct. 2008, pp. 601-606, vol. 5.
Hrafuji, Naoe et al., miR-411 is Up-Regulated in FSHD myoblasts and suppresses myogenic factors, Orphanet Journal of Rate Diseases, 2013, 8:55.
Dutt, Vikas et al., Skeletal muscle atrophy: Potential therapeutic agents and their mechanisms of action, Pharmacological Research 99, 2015, pp. 86-100.
Kang, Peter B. et al., Advances in Musclar Dystrophies, JAMA Neurology, Jul. 2015, pp. 741-742, vol. 72, No. 7.
Shieh, Perry B., Muscular Dystrophies and Other Genetic Myopathies, Neurol Clin 31 (2013) pp. 1009-1029.

* cited by examiner

*Primary Examiner* — Layla Soroush
(74) *Attorney, Agent, or Firm* — Lewis Rice LLC

(57) ABSTRACT

The use of BETi as a potential treatment for FSHD is provided. Specifically, the use of BETi, and particularly selective BETi for BRD4, are shown to inhibit DUX4 expression which is expected to result in a decrease in the severity of symptoms of FSHD. Further, the treatments are shown to work when pulsed as opposed to continuous. This allows for a BETi to be supplied to a human in a pulse, and then allows the human to not need any additional treatment for a window at least as long as the one of the treatment pulse.

11 Claims, 13 Drawing Sheets

INHIBITION OF DUX4 EXPRESSION USING BROMODOMAIN AND EXTRA-TERMINAL DOMAIN PROTEIN INHIBITORS (BETI)

CROSS REFERENCE TO RELATED APPLICATION(S)

This application claims benefit of U.S. Provisional Patent Application Ser. No. 61/880,565, filed Sep. 20, 2013, the entire disclosure of which is herein incorporated by reference.

BACKGROUND

1. Field of the Invention

Discussed herein are systems and methods for the inhibition of bromodomain and extra-terminal domain (BET) proteins to block induction of DUX4 mRNA and protein expression activity and assist in treatment of facioscapulohumeral muscular dystrophy (FSHD).

2. Description of the Related Art

Facioscapulohumeral muscular dystrophy (FSHD) is one of the most common type of muscular dystrophy (akin in prevalence to Duchenne muscular dystrophy and myotonic dystrophy) affecting approximately 12 in 100,000. It is a genetic muscle disorder that initially affects the muscles of the face, shoulder blades and upper arms. However, muscle degeneration is progressive and spreads to other muscles including those in the legs and hips. The disorder is most commonly detected due to muscle weakness in the shoulder blades resulting in muscles that no longer serve to correctly support the shoulder blades as a fulcrum for the arm. Thus, the shoulder blades often have excessive movement which can result in difficulty throwing or raising the arms above the head. Weakness of facial muscles resulting in difficulty puckering (and related activities such as drinking through a straw or whistling) are also common.

FSHD usually begins prior to age 20 and the disorder is progressive with muscle degeneration continuing throughout life. Sometimes FSHD is divided between adult-onset and infantile-onset forms with the adult onset (which includes onset in adolescence) being more common. Because it is characterized by progressive muscle weakness, in some individuals muscle weakness will eventually spread to the lower extremities, often resulting in affected individuals becoming wheelchair-bound. Further, pain and fatigue are frequent complaints and are presumably associated with muscle degeneration.

FSHD is almost always associated with a genetic flaw (mutation) that leads to a shorter than usual segment of DNA on chromosome 4. Specifically, FSHD type 1 (FSHD1) accounts for 95% of FSHD cases and is associated with contraction of the number of D4Z4 repeat units in the macrosatellite array at 4q35. FSHD2 (~5% of cases) occurs in the absence of D4Z4 contraction and is believed caused by haplo-insufficiency or mutation of the SMCHD1 gene. Symptoms and effects of both types are generally the same.

The polymorphic D4Z4 array varies between 11 and >100 copies in healthy individuals, while FSHD1 patients retain 1-10 repeat units. Each repeat unit contains a copy of the DUX4 retrogene. While the disorder is believed to be genetically passed on, it also may occur spontaneously in certain cases.

There is currently no treatment available for FSHD and no clinical trials of promising treatments are ongoing. Nonsteroidal anti-inflammatories, or NSAIDs, are sometimes prescribed to provide comfort and mobility, but they have no effect on the underlying disease. Similarly, orthoses are often used to help support parts of the body where muscle degeneration is resulting in insufficient support, and certain types of surgery such as thoracoscapular fusion, where the shoulder blade is fused to the ribs to provide for more rigid support for the arms, are used in similar fashion. While these options can often increase mobility and function, they also have no effect on the underlying degeneration and therefore serve only to provide for comfort, as opposed to cure.

Despite recent advances in our understanding of the epigenetic mechanism of FSHD pathology, little insight has been gained into specific therapeutic targets amenable to small molecule drug intervention. Drug intervention can be beneficial for disorders such as FSHD as it can be significantly less invasive than surgery and, should it be able to target an underlying cause of the degeneration, can potentially further slow, halt, or possibly reverse the degeneration itself. Druggable targets that regulate DUX4 expression and evaluation of the therapeutic potential of the corresponding inhibitory compounds are desirable.

SUMMARY

The following is a summary of the invention in order to provide a basic understanding of some aspects of the invention. This summary is not intended to identify key or critical elements of the invention or to delineate the scope of the invention. The sole purpose of this section is to present some concepts of the invention in a simplified form as a prelude to the more detailed description that is presented later.

The use of BET bromodomain protein inhibitors (BETi) as a potential treatment for FSHD is provided. Specifically, the use of BETi, and particularly selective BETi for BRD4, are shown to inhibit DUX4 expression which is expected to result in a decrease in the severity of symptoms of FSHD. Further, the treatments are shown to work when pulsed as opposed to continuous. This allows for a BETi to be supplied to a human in a pulse, and then allows the human to not need any additional treatment for a window at least as long as the one of the treatment pulse.

There is described herein, among other things, a method of reducing muscular weakness from facioscapulohumeral muscular dystrophy (FSHD), the method comprising: administering to a patient with FHSD a therapeutic quantity of a BET inhibitor (BETi) sufficient to reduce DUX4 expression in said patient.

In an embodiment of the method, the BETi is selected from the group consisting of: (+)-JQ1, PFI-1, I-BET-762, I-BET-151, RVX-208, and CPI-0610.

In an embodiment of the method, the BETi is a selective inhibitor of BRD2.

In an embodiment of the method, the BETi is a selective inhibitor of BRD4.

In an embodiment of the method, the BETi is a broad spectrum inhibitor.

In an embodiment of the method, in said administering, said BETi is provided in an initial dose and a second dose is not provided for at least 24 hours after said initial dose is finished.

In an embodiment of the method, said initial dose is provided continuously over 24 hours.

In an embodiment of the method, in said administering, said BETi is provided in an initial dose and a second dose is not provided for at least 48 hours after said initial dose is finished.

In an embodiment of the method, in said administering, said BETi is provided in an initial dose and a second dose is not provided for at least 72 hours after said initial dose is finished.

In an embodiment of the method, in said administering, said BETi is provided in an initial dose and a second dose is not provided for at least 96 hours after said initial dose is finished.

In an embodiment of the method, the patient is human.

BRIEF DESCRIPTION OF THE DRAWINGS

FIG. 8A shows the level of ZSCAN4, and FIG. 8B shows the level of TRIM43. FSHD1 (54-2) or normal (54-6) myoblasts were treated with DMSO (control) or compounds (+)-JQ1 (500 nM) or PFI-1 (2 µM) as indicated for 48 hours before RNA isolation. mRNA levels are normalized to the FSHD1 cells DMSO control using RPL13A as the internal control.

FIG. 9A shows the ZSCAN4 mRNA levels after treatment with (+)-JQ1 for 24, 48, and 72 hours. FIG. 9B shows the ZSCAN4 mRNA levels after treatment with BETi (+)-JQ1, I-BET762 and I-BET151 for 72 hours at the indicated concentrations.

FIG. 10A shows results using FSHD1 myoblasts. FIG. 10B shows results using FSHD2 myoblasts.

FIG. 14A shows the timeline. Subconfluent myoblasts were treated I-BET762 (Cmpd) for either 8, 24, 48 or 72 hours and gene expression analyzed at the 72 hour time point. FIGS. 14B, 14D, and 14F show DUX4 target gene expression determined by qRT-PCR. FIGS. 14C, 14E, and 14G shown non-DUX4 target gene expression.

FIG. 15A shows the experimental timeline. FSHD1 myoblasts were treated with a range of concentrations of I-BET762 for 24 hours. Compound was then removed, the cells rinsed once with growth media and fresh media re-applied to cells. RNA was harvested at days 3, 4, 6, and 8 as indicated for analysis by qRT-PCR. FIG. 15B shows ZSCAN4 RNA levels versus I-BET762 concentration and FIG. 15C shows MBD3L2 RNA levels versus I-BET762 concentration. $EC_{50}$ curves were plotted at each time point.

FIG. 16A shows ZSCAN4 RNA levels and FIG. 16B shows Myosin heavy chain (MYH2) RNA levels.

DESCRIPTION OF THE PREFERRED EMBODIMENT(S)

Figure 1:
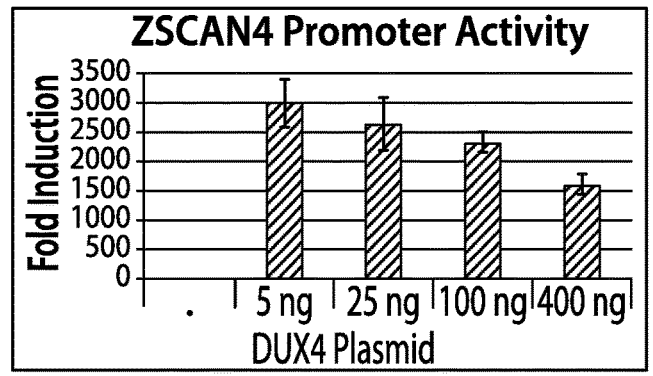
FIG. 1 shows a graph indicating that DUX4 expression strongly induces the ZSCAN4 promoter. A luciferase reporter plasmid containing the promoter and enhancer from the ZSCAN4 gene was transfected into normal myoblasts in the absence or presence of a DUX4 expression plasmid. Results are expressed as fold increase in luciferase activity normalized to the activity of the ZSCAN4 reporter in the absence of exogenous DUX4 expression with error bars indicating standard deviations.

Discussed herein is the use of a cell based assay to detect DUX4 expression in FSHD muscle cells. The connection of DUX4 expression to FSHD is used to screen a library of compounds that target epigenetic modifier proteins to locate a potential treatment for FSHD. This "chemical genetics" approach identified the bromodomain and extra terminal (BET) family of proteins as key targets involved in DUX4 expression. Selective inhibitors of BET proteins (BETi), specifically (+)-JQ1, PFI-1, RVX-208 (Resverlogix Corp.), I-BET-762 (GlaxoSmithKline), and I-BET-151 (GlaxoSmithKline) were found to block the induction of DUX4 and its downstream targets ZSCAN4 and TRIM43 during differentiation of FSHD1 and FSHD2 muscle cells in vitro.

Further, BETi also block DUX4 expression in undifferentiated FSHD myoblasts. While this disclosure will focus on the use of JQ1 and certain other BETi, it should be recognized that specific BETi can be used in a variety of different situations and a large number of potential BETi are known. This includes using BETi such as, but not limited to, those described in *BET bromodomain inhibitors: a patent review* Garnier et al. (informa healthcare (2014)) the entire disclosure of which is herein incorporated by reference.

Also, ZSCAN4 and TRIM43 mRNA levels were analyzed 48 to 72 hours after the BETi was added. Cells grown continuously in a low dose BETi JQ1 exhibited a greater than 95% reduction in steady state levels of ZSCAN4 mRNA and this effect was sustained, requiring longer than 7 days to recover after removal of JQ1 from the cultures. This data suggests that BETi generally and (+)-JQ1, PFI-1, I-BET-762 (GlaxoSmithKline), and I-BET-151 (GlaxoSmithKline) specifically, have therapeutic value in FSHD. RVX-208 (Resverlogix Corp.) and CPI-0610 (Constellation Pharmaceuticals) as BETi are also expected to have therapeutic value in FSHD.

Muscle pathology in both FSHD1 and FSHD2 coincides with the epigenetic de-repression of the normally silent DUX4 gene. In healthy individuals, DUX4 is expressed early in development but then becomes silenced in somatic cells as part of sub-telomeric heterochromatin. DUX4 is a double-homeobox transcription factor and its abnormal expression in FSHD individuals initiates a transcriptional program that results in muscle cell dysfunction and death. Although the genetic defects differ in FSHD1 and FSHD2, the clinically indistinguishable outcomes indicate a convergence in pathways responsible for DUX4 expression. Chromatin is de-condensed at 4q35 in muscle cells from both FSHD1 and FSHD2 patients; however, DUX4 expression is variegated and an extremely rare event in vivo and in vitro. Less than 1 in 1000 FSHD myoblasts in culture express DUX4 in stochastic "bursts" of expression. The proportion of nuclei exhibiting bursts of DUX4 expression increases upon myotube differentiation.

It is believed that a number of events subsequent to general chromatin de-condensation occur to fully de-repress DUX4. Therefore, knowledge of the epigenetic mechanisms behind the bursts of DUX4 expression allows for the development of therapeutic strategies to maintain the repressed state of the DUX4 gene. Specifically, the use of inhibitors of BET proteins (BETi) would appear to provide therapeutic effects to those with FSHD by silencing of DUX4 expression.

Recent work has identified Polycomb group (PcG) repression as the key mechanism governing the silencing of DUX4 and has implicated Trithorax group (TrxG) mechanisms in de-repression. PcG and TrxG proteins are evolutionarily-conserved complexes originally identified in *Drosophila* that regulate chromatin structure and are required to maintain established gene expression patterns (i.e. epigenetic memory). PcG proteins comprise two major enzymatic complexes whose activities contribute to chromatin compaction: Polycomb repressive complex 1 (PRC1) and PRC2. PRC1 contains an E3 ubiquitin ligase and catalyzes ubiquitination of lysine 119 on histone H2A. PRC2 catalyzes the di- and tri-methylation of lysine 27 on histone H3 (H3K27 me2/me3). TrxG proteins encompass a variety of biochemical activities including chromatin remodeling, histone modification, and transcription factor (trans-activating) functions that antagonize PcG proteins to de-repress PcG targets. How TrxG proteins counteract PcG repression is not fully understood, but has been recognized. In *Drosophila*, two histone methyltransferases that are part of TrxG complexes, absent, small or homeotic discs 1 (ASH1) and trithorax (TRX) are thought to counteract PcG silencing through histone methylation activity, though some have challenged this simple view.

PcG and TrxG bind to specific DNA regions termed Polycomb/Trithorax response elements (PREs/TREs) in *Drosophila*. Each human D4Z4 repeat contains multiple elements that correspond to *Drosophila* PREs, and PcG-mediated repression of 4q35 genes appears to depend on D4Z4 copy number. Recently, new insights into how TrxG proteins are involved in overcoming PcG repression to de-repress DUX4 gene expression have been uncovered. ASH1L, the mammalian homolog of fly ASH1, was shown to be recruited to D4Z4 specifically in FSHD myoblasts by the D4Z4-encoded long noncoding RNA (ncRNA) DBE-T. ASH1L recruitment was associated with an increase in H3K36me2 and DUX4 de-repression. However, the full mechanism by which DBE-T and ASH1L functions to de-repress DUX remains to be elucidated.

Epigenetic modifications controlling chromatin compaction and access to regulatory factors include DNA methylation and post-translational modifications of histones including methylation, acetylation, ubiquitination and phosphorylation. Additionally, a number of noncoding RNAs, such as DBE-T described above, play a role as epigenetic modifiers. FSHD is considered an "epigenetic disease" due to the fact that chromatin at D4Z4 is de-condensed and exhibits correspondingly altered epigenetic marks including loss of DNA methylation, decreased H3K9me3 with decreased heterochromatin protein 1 gamma and cohesin binding, and decreased PcG silencing mark H3K27me3 specifically at contracted D4Z4 alleles. These epigenetic modifications are processed by a large number of "epigenetic modifiers" that are broadly classified by their functions as "writers," "readers" and "erasers" that, respectively, add, detect by binding, or remove various chemical modifications.

The specific marks altered in disease states such as FSHD provide information as to the epigenetic machinery that is most closely involved with the disease process. For example, decreased enrichment for the H3K27me3 mark implicates a defect in PcG silencing while increased H3K36me2 suggests TrxG activation. Another approach to gain information about disease states is to screen compounds that inhibit defined targets (chemical genetic probes) against disease-relevant biological assays. Recent advances towards epigenetic interventions for cancer and other diseases have resulted in the development of many novel chemical probes. These include marketed drugs, compounds in clinical trials and many other compounds that target specific proteins whose signals contribute to epigenetic gene regulation. The availability of chemical modulators of epigenetic targets provides a unique opportunity to identify novel pathways relevant to FSHD. Applying these reagents in a "chemical genetics" approach helps define the mechanism of aberrant gene regulation in FSHD and lead to therapeutic interventions that address the underlying epigenetic mechanism of pathology.

The germline transcription factor DUX4 induces a complex pattern of inappropriate gene expression in FSHD muscle, including activation of early stem cell and germline programs. A complicating factor is that DUX4 can only be detected in approximately 1 in 1000 myoblasts in vitro, making DUX4 mRNA difficult to detect. However, the downstream targets of DUX4, most of which are undetectable in normal myoblasts, are readily detectable in FSHD myoblasts. One of these DUX4 target genes, ZSCAN4, contains 4 tandem DUX4 binding sites within its enhancer/promoter region. A luciferase reporter vector containing the enhancer/promoter region from ZSCAN4 can serve as a sensitive indicator of DUX4 expression and, indirectly, the chromatin state at the DUX4 locus. FIG. 1 shows a ca. 3000-fold induction of the ZSCAN4 luciferase reporter in co-transfection experiments with a DUX4 expression plasmid in myoblasts. These data indicate that the ZSCAN4 luciferase reporter is highly sensitive to exogenously expressed DUX4.

Figure 2:
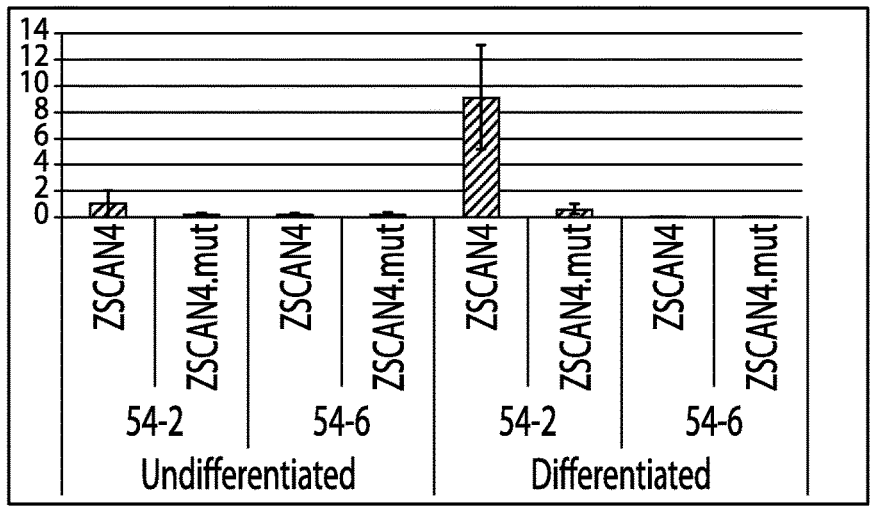
FIG. 2 shows a graph indicating that the ZSCAN4 promoter is induced by myoblast differentiation only in FSHD (54-2) but not normal (54-6) myotubes. In addition, ZSCAN4 promoter induction requires the presence of DUX4 binding sites since mutation of these sites (ZSCAN4.mut) blocks promoter induction. Results are expressed as fold increase in luciferase activity normalized to the activity of the ZSCAN4 reporter in undifferentiated FSHD myoblasts.

To test responsiveness to endogenously expressed DUX4, the wt ZSCAN4 reporter or a mutant reporter in which 3 of the 4 DUX4 binding sites were mutated and were transfected into FSHD1 (54-2) and control (54-6) myoblasts derived from a mosaic patient. The wt ZSCAN4 luciferase reporter elicited only weak and sporadic activity in undifferentiated FSHD myoblasts (not shown). Based on observations that DUX4 is induced when myoblasts differentiate to myotubes, undifferentiated cells to those induced to differentiate for 6 days were compared. FIG. 2 shows that ZSCAN4 promoter activity is induced about 10-fold upon differentiation of FSHD1 but not control myoblasts. In addition, this induction requires intact DUX4 binding sites since the mutant reporter was not equally induced. Similar results are obtained when using FSHD2 cells (not shown). Together, these data suggest that ZSCAN4 reporter readout represents the de-repression of DUX4 expression that occurs only in the context of an FSHD genetic background.

Figure 3A:
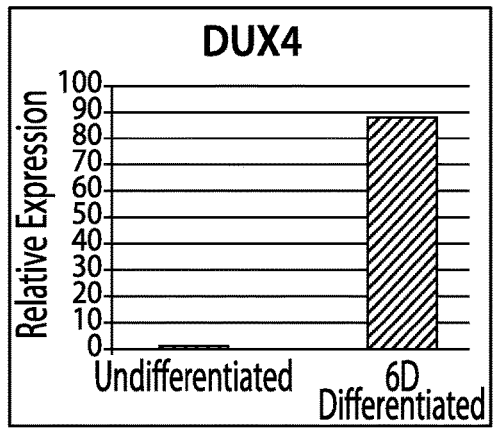
FIGS. 3A and 3B show graphs indicating that DUX4 and ZSCAN4 mRNA levels are induced during FSHD1 myoblast differentiation. Results are expressed as relative expression normalized to levels in undifferentiated cells which were set to one.
Figure 3B:
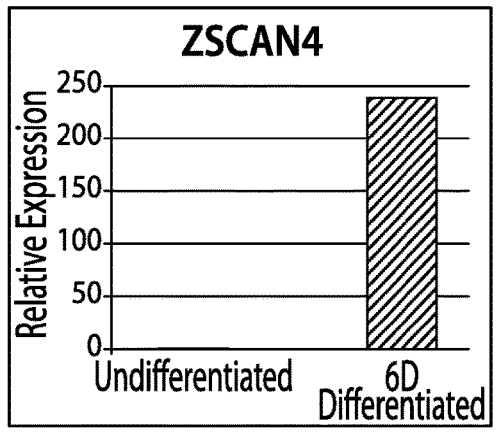

To confirm that the increase in ZSCAN4 luciferase reporter readout mirrored an increase in DUX4 and ZSCAN4 expression, mRNA from duplicate samples was isolated and analyzed by qPCR. As mentioned above, DUX4 message is expressed only in a small subset of cells and is difficult to detect. In addition, two forms of the mRNA are present, a non-protein coding short form that is present in both normal and FSHD muscle cells (DUX4s) and a DUX4-encoding full length form (DUX4fl). A TaqMan-style qPCR assay to specifically detect DUX4fl was not available and an assay detecting both DUX4s and DUX4fl was used for detecting the increase in DUX4fl that accompanies FSHD myotube differentiation. FIGS. 3A and 3B show that under the conditions of the screening assay, DUX4 mRNA levels are induced nearly 90-fold upon myoblast differentiation and ZSCAN4 mRNA levels are induced greater than 200-fold. These data indicate that the screening assay does report bona fide DUX4 de-repression and associated ZSCAN4 induction.

Based on the above, differentiation of FSHD myoblasts and a concomitant increase in ZSCAN4 promoter activity represent a model of DUX4 de-repression that is amenable to screening compounds. Two small libraries of compounds targeting known epigenetic modifying enzymes were obtained: Cayman Chemicals "Epigenetic Screening Library" and Selleck Chemicals "Epigenetic Compound Library". Together they represent about 100 modulators of known epigenetic "writer", "reader" and "eraser" proteins. These compounds were screened for their activity in modulating the induction of ZSCAN4 promoter activity in differentiating FSHD myoblasts. A co-transfected internal control plasmid that expressed Renilla luciferase was used to monitor general compound toxicities as well as non-specific transcriptional effects. There were six categories of "hits" identified as blocking the induction of Firefly luciferase (ZSCAN4 reporter) without significantly inhibiting Renilla luciferase activity (control).

Figure 4:
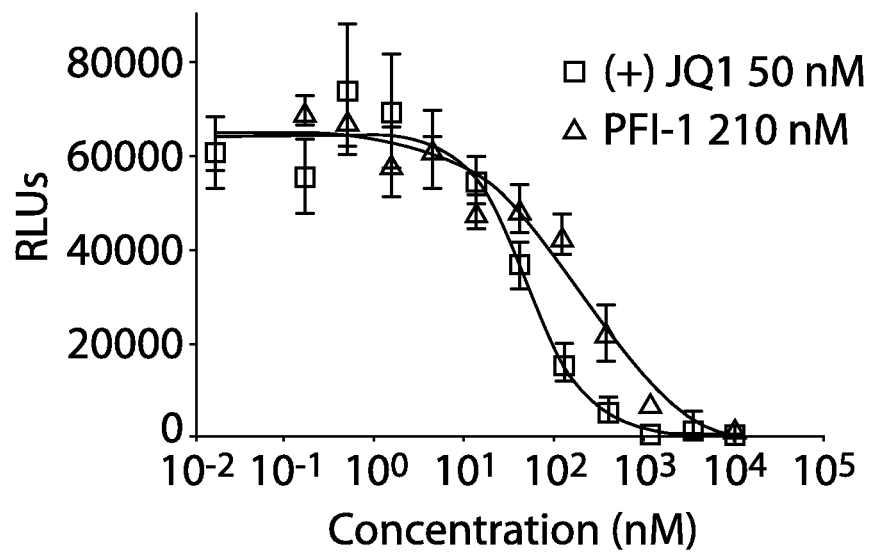
FIG. 4 shows a graph of the inhibition of ZSCAN4 promoter activity in differentiated FSHD myoblasts by BETi (+)-JQ1 and PFI-1. Results are expressed as relative luciferase units (RLUs) with $IC_{50}$s indicated. Note that concentration is plotted on a log scale.

Notably, materials generally identified as BET bromodomain inhibitors (BETi) (2 separate hits) resulted in nearly complete inhibition of ZSCAN4 promoter induction and would likely treat or help eliminate symptoms of FSHD. Inhibition curves for the BET bromodomain inhibitor (+)-JQ1 and PFI-1 are shown in FIG. 4. The $IC_{50}$s are consistent with reported cellular assay potencies for each compound. Additionally, these inhibitors were active in both FSHD1 and FSHD2 myoblasts, suggesting that they act at a point in the epigenetic switch controlling DUX4 expression common to both genetic defects.

Figure 5:
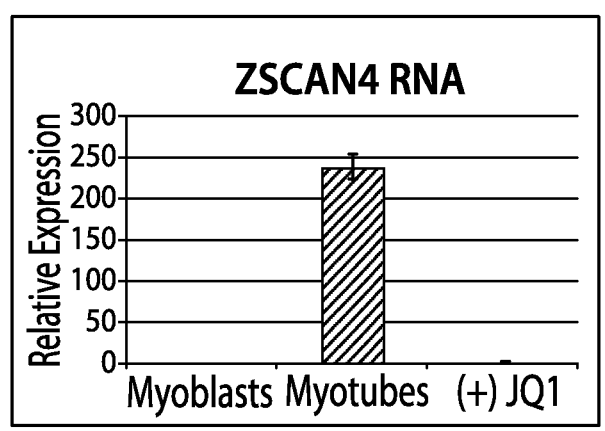
FIG. 5 shows a graph of ZSCAN4 mRNA levels determined by qRT-PCR in undifferentiated FSHD1 myoblasts, 6 day differentiated myoblasts and differentiated myoblasts treated with (+)-JQ1. Error bars indicate standard deviations.

The reporter readout in the screening assay is designed to reflect the endogenous response of the ZSCAN4 promoter. Thus, an important secondary assay is to confirm that screening hits block the induction of endogenous ZSCAN4 mRNA. TaqMan qRT-PCR was used to measure ZSCAN4 mRNA levels after compound treatment of differentiating FSHD1 myoblasts. The endogenous control mRNA chosen for normalization was the ribosomal protein L13A (RPL13A). FIG. 5 shows that the BETi (+)-JQ1 blocks induction of ZSCAN4 mRNA upon differentiation of FSHD myoblasts. Similar results were seen for each compound when using FSHD2 myoblasts. Additionally, the levels for another DUX4-induced gene, TRIM43 were measured. Similar to ZSCAN4, TRIM43 mRNA was induced by differentiation of FSHD myoblasts and its induction blocked by (+)-JQ1 (not shown), providing evidence that this compound blocks multiple downstream targets of DUX4 and therefore is suitable for use as a therapy for FSHD.

Figure 6:
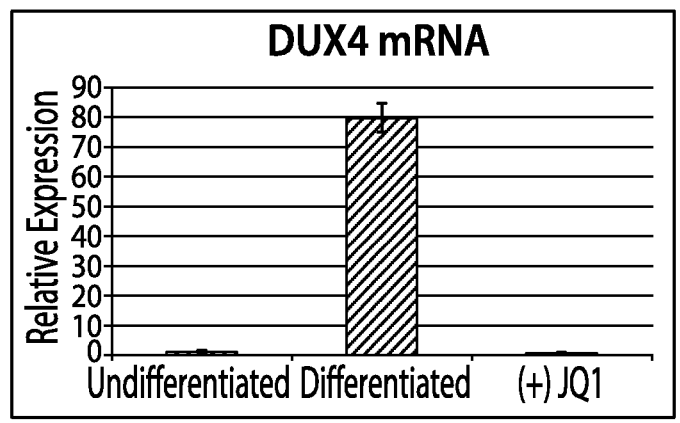
FIG. 6 shows a graph indicating that (+)-JQ1 inhibits the induction of DUX4 mRNA by differentiation. Error bars indicate standard deviations.
Figure 7:
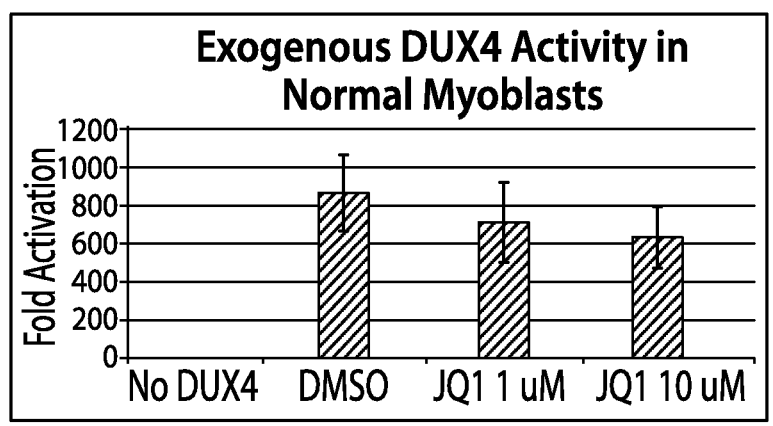
FIG. 7 shows a graph indicating that DUX4 activity is not blocked by (+)-JQ1. A DUX4 expression plasmid was co-transfected with the ZSCAN4 reporter plasmid and cells immediately treated with compound. Results are normalized to activity in the absence of exogenously expressed DUX4.

While not intending to be limited by any theory of operation, blocking induction of ZSCAN4 mRNA may occur by one of several mechanisms: i) blocking de-repression of DUX4, ii) interfering with DUX4 activity subsequent to its de-repression and iii) via a DUX4-independent mechanism. Levels of DUX4 mRNA by qRT-PCR in the samples from compound treatment were measured. FIG. 6 demonstrates that (+)-JQ1 blocks the induction (de-repression) of DUX4 mRNA that accompanies differentiation of FSHD1 myoblasts. Similar results are seen when using FSHD2 myoblast (not shown). To ensure that (+)-JQ1 did not interfere with DUX4 activity, a co-transfection experiment was performed in which the ZSCAN4 luciferase reporter construct was transfected into normal myoblasts along with a DUX4 expression plasmid similar to the experiment in FIG. 1. Three hours after transfection was started, (+)-JQ1 was added at concentrations up to twenty fold higher than needed to completely block DUX4 de-repression in the differentiation model. Cells were harvested for luciferase activity 24 hours later. FIG. 7 demonstrates that even at a 10 μM concentration, (+)-JQ1 had only a marginal (not statistically significant) effect on DUX4 activity. These data further support that (+)-JQ1 inhibits the expression of DUX4 rather than its activity.

Based on the above, there is an about 90-fold induction of DUX4 mRNA upon differentiation of FSHD myoblast for 6 days. The compound (+)-JQ1 appears to block this induction. Since the induction of DUX4 coincides with muscle cell differentiation, it is possible that (+)-JQ1 acts indirectly by blocking muscle cell differentiation. (+)-JQ1 affected markers of muscle cell differentiation, however, particularly inhibiting the appearance of the late differentiation marker myosin heavy chain (MYH2).

By testing the effects of (+)-JQ1 in undifferentiated myoblasts, it is possible to avoid the complication of inhibiting the muscle differentiation program. Undifferentiated FSHD1 myoblasts were treated with the BETi (+)-JQ1 or PFI-1 for 24 and 48 hours and a qRT-PCR was performed to determine mRNA levels for DUX4, ZSCAN4 and TRIM43. As noted before, the TaqMan primer/probe set detects both DUX4s (expressed in normal and FSHD myoblasts, non-protein encoding) and DUX4fl (expressed only in FSHD myoblasts, DUX4-encoding). Since DUX4fl is expressed at hard to detect levels in undifferentiated FSHD myoblasts, qPCR signals representing the short DUX4 message, or D4Z4 transcripts from other genomic regions present at very low levels interfere with the signal for DUX4fl and make direct qPCR difficult.

Figure 8A:
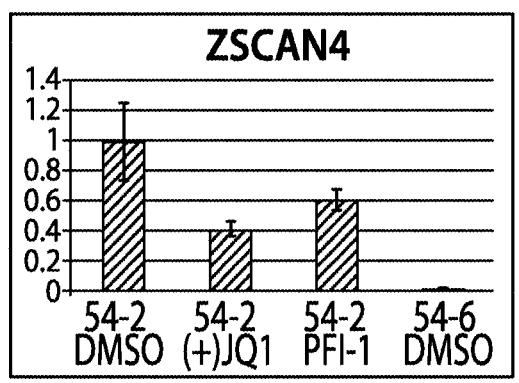
FIGS. 8A and 8B show graphs of the levels of mRNA for ZSCAN4 and TRIM43 (downstream targets for DUX4) in undifferentiated myoblasts.
Figure 8B:
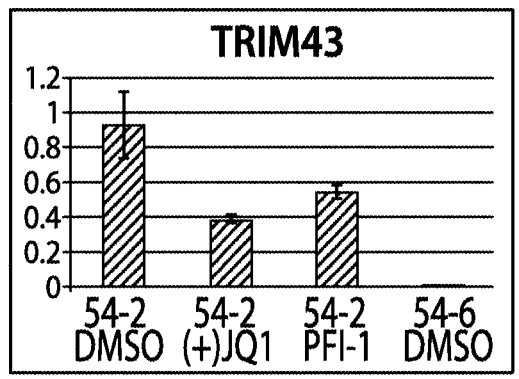
Figure 9A:
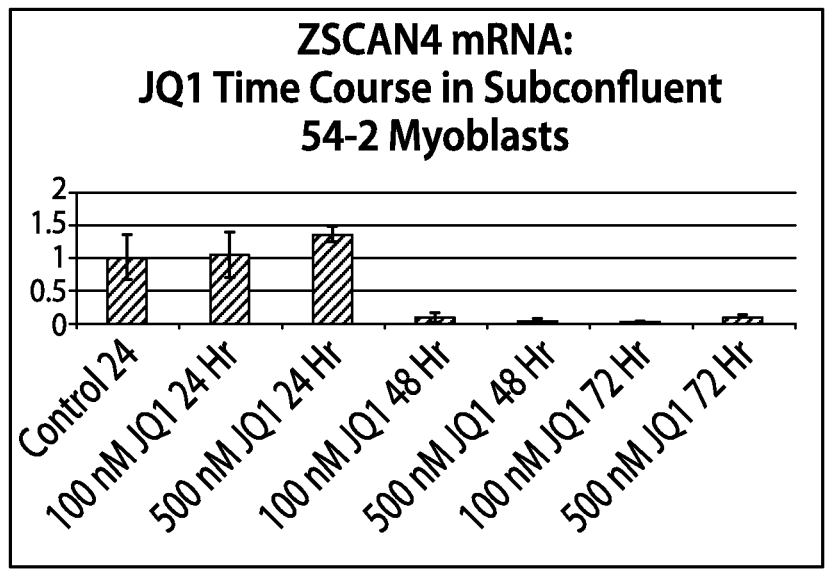
FIGS. 9A and 9B show graphs of the levels of ZSCAN4 mRNA after treatment of subconfluent FSHD1 myoblasts with BETi.

Therefore, a more sensitive and accurate indicator of DUX4 expression in undifferentiated FSHD myoblasts is the amplified signal of its downstream targets ZSCAN4 and TRIM43. FIGS. 8A, and 8B show that the levels of ZSCAN4 and TRIM43 are significantly decreased by 48 hour treatment with both (+)-JQ1 and PFI-1, suggesting that blocking the expression of DUX4 with BETi is independent of muscle cell differentiation. Interestingly, the kinetics of the response appears to be slow since there was no decrease with 24 hours of compound treatment detected (FIG. 9A). While not intending to be bound by any theory of operation, it is hypothesized that BETi blocks the de-repression of DUX4 that occurs stochastically at a very low frequency in undifferentiated myoblasts. The expression of downstream targets is sustained such that decreases in their mRNA levels require blocking new DUX4 expression over the course of a longer time frame (e.g. 48 hours or more). The experiment depicted in FIGS. 8A, 8B, and 8C was performed in semi-confluent monolayers of FSHD1 myoblasts. These results demonstrated that two BETi (PFI-1 and (+)-JQ1) reduce the expression of DUX4 downstream targets ZSCAN4 and TRIM43 after 48 hours of treatment, excluding the possibility that inhibition of DUX4 expression is dependent on differentiation. Longer term exposure to (+)-JQ1 results in a more dramatic decrease in the expression of downstream targets (as shown in FIGS. 9A-10B).

Figure 9B:
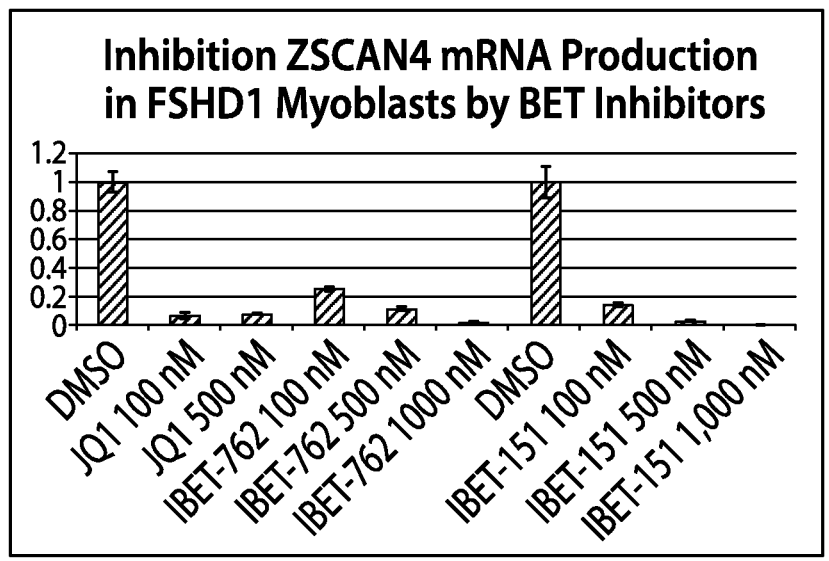

FIG. 9A shows a time course of ZSCAN4 mRNA levels during treatment of subconfluent FSHD1 myoblasts with (+)-JQ1. Under these conditions, dramatic (>95%) decreases in ZSCAN4 mRNA are evident at both 48 hours and 72 hours of compound treatment suggesting that effects of BETi on ZSCAN4 mRNA occur faster in dividing cells. FIG. 9B shows the effects of additional BETi (I-BET762, I-BET151) on ZSCAN4 mRNA levels in subconfluent FSHD1 myoblasts after 72 hours treatment. These data emphasize the general nature of BET inhibition to reduce ZSCAN4 mRNA levels presumably through inhibition of the production of DUX4.

Figure 10A:
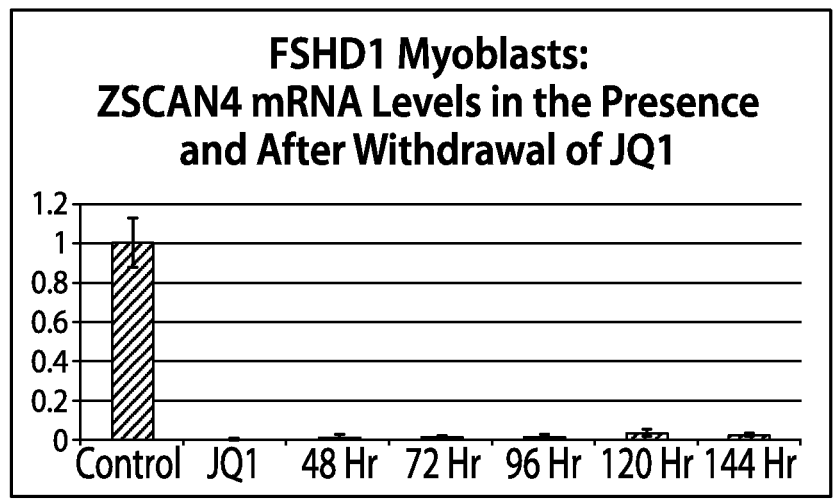
FIGS. 10A and 10B show graphs of the levels of ZSCAN4 mRNA after growth of FSHD myoblasts in the presence of low concentration (+)-JQ1 (100 nM) and during a time course after withdrawal of (+)-JQ1.
Figure 10B:
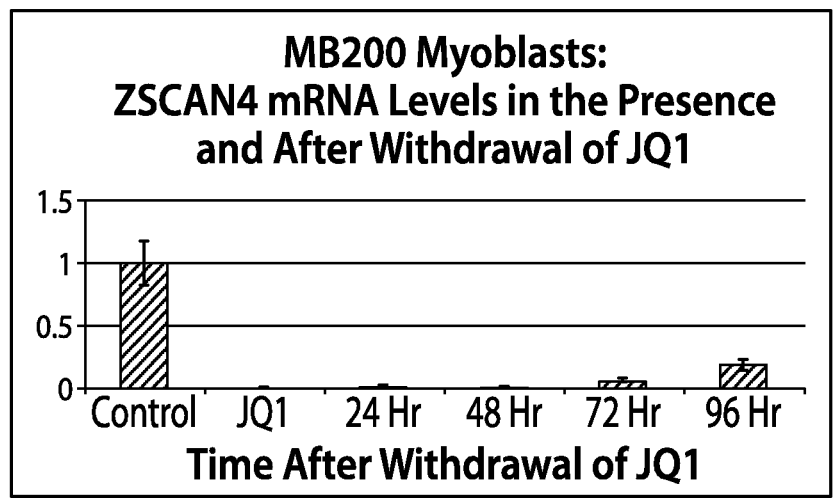
Figure 11A:
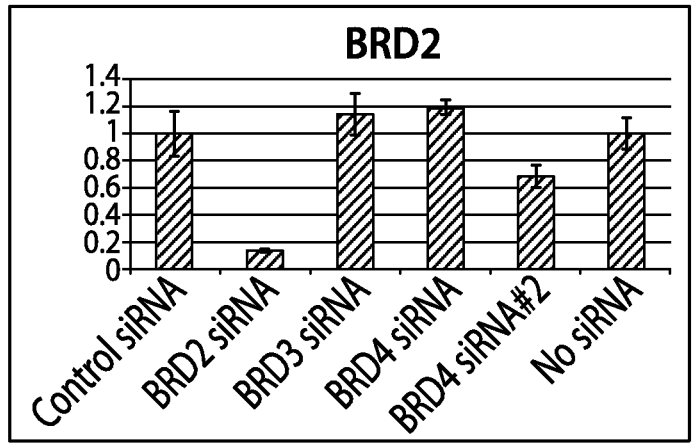
FIGS. 11A, 11B, and 11C show siRNA knockdown of BET family members in FSHD myoblasts. FSHD1 myoblasts were transfected with the indicated siRNAs and RNA analyzed 96 h later by qRT-PCR.
Figure 11B:
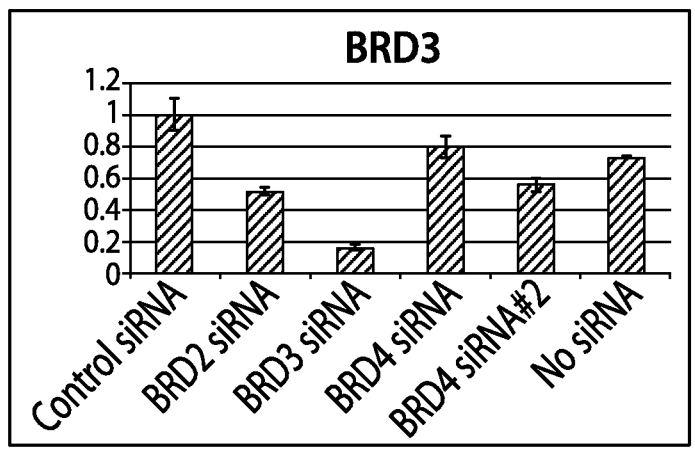
Figure 11C:
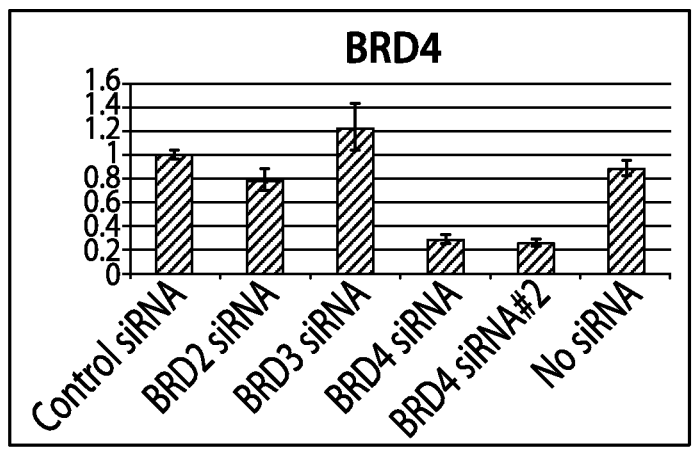
Figure 12:
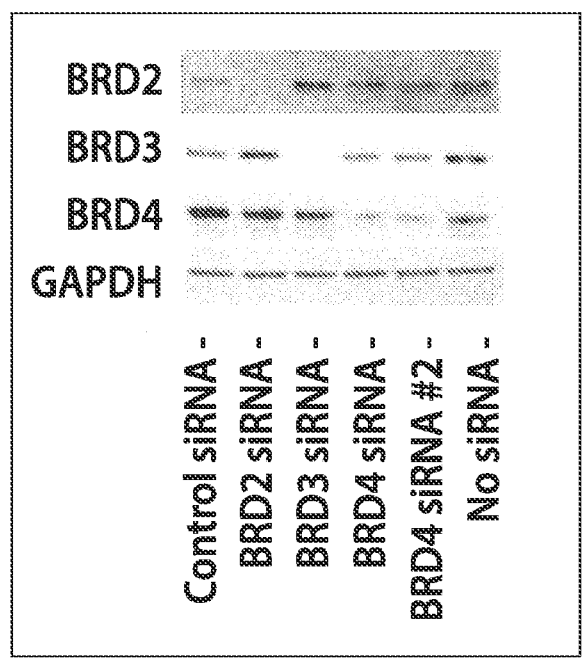
FIG. 12 shows BET family protein levels after siRNA knockdown. Cells were transfected as above and 72 h later cell lysates were analyzed by western blot with the indicated antibodies.

A complimentary set of experiments was conducted in undifferentiated myoblasts to determine if treatment options with BETi could have lasting effects on DUX4 inhibition even after treatment ceased. TO further clarify the utility of BET inhibition, FSHD1 and FSHD2 (MB200) myoblasts were grown continuously in low dose (100 nM) (+)-JQ1. ZSCAN4 mRNA levels were measured at the steady state level during growth in low dose (+)-JQ1 and during a time course after withdrawal of (+)-JQ1 from the cultures. FIG. 10A shows a graph of the levels of ZSCAN4 mRNA in FSHD1 myoblasts. The levels of ZSCAN4 mRNA remained decreased >95% compared to control FSHD1 myoblast for 144 hours (6 days). FIG. 10B shows a graph of the levels of ZSCAN4 mRNA in FSHD2 myoblasts. The levels of ZSCAN4 remained decreased >95% compared to control FSHD1 myoblast for 72 hours (3 days) and were still decreased by 75% at 96 hours after withdrawal of (+)-JQ1 from the cultures. These data indicate an extended pharmacodynamic effect of BET inhibition that perhaps relates to the slow stochastic nature of the induction of DUX4 expression. This suggests that BETi may have a favorable therapeutic profile in that their pharmacodynamic effects (decreased DUX4 and downstream targets like ZSCAN4) are extended relative to their pharmacokinetic profile (physical presence of drug).

(+)-JQ1 is generally accepted to inhibit the activity of all four mammalian BET bromodomain proteins (BRD2, BRD3, BRD4 and BRDt). Therefore, inhibition of at least one of the four mammalian BET bromodomain proteins would appear to have a positive effect on FSHD. In an embodiment, general inhibition of BET can be a useful treatment for FSHD and any BETi can be used. However, it is known that broad spectrum BETi often produce undesirable immunosuppressive effects which can lead to secondary infection and their use can lead to complicating side effects such as diarrhea.

Because of the above concerns, while one embodiment of the present invention provides that a broad spectrum BETi can be used to treat the effects of FSHD, it is desirable to locate alternatives that may have fewer side effects. In an embodiment, this can be accomplished through the use of a selective BETi which targets only a subset of the relevant BET, ideally only one or two. Further, it may alternatively or additionally be desirable to be able to provide a BETi in a limited dose and then remove it so long as the DUX4 expression remains inhibited. Such a treatment plan can reduce general immunosuppressive effects allowing a patient's system to recover between treatments. BETi have traditionally always been used with continuous or near continuous treatments (e.g. treatments twice a day, every day) and a treatment plan involving a single treatment, and then a long waiting period are generally unknown. The above, may achieve a similar effect in reducing DUX4, while reducing undesirable side effects.

While it is believed that general inhibition is suitable in an embodiment, in an alternative embodiment a combination of RNAi knockdowns and forced expression can be used to determine the specific BET bromodomain family members whose inhibition results in blocking induction of DUX4 and its targets to allow for more accurate targeting of compounds, should such compounds become available and reduction of side effects. Initially, determining the expression of all four BET genes at the mRNA and protein levels in both normal and FSHD myoblasts in undifferentiated cells and during the course of differentiation can be accomplished. This information alone may provide sufficient detail for further refinement. For example, if the expression of one of the BET proteins increasing with differentiation can correlate with DUX4 de-repression. The expression of BRD2, BRD3 and BRD4 is considered universal while, interestingly, BRDt is considered testis-specific and therefore also provides for a further therapeutic possibility. The fact that forced DUX4 expression in vitro, FSHD muscle cells in vitro and FSHD patient muscle biopsies are all associated with aberrant male germline gene expression patterns is intriguing in light of the fact that BRDt is a testis-specific BET protein whose function is required for male germline gene expression. This initially implies that a BETi specific to BRDt also may be a suitable therapeutic.

In order to determine which gene target of BETi (BRD2, BRD3, BRD4, or BRDt) are necessary for DUX4 expression, and are thus therapeutic targets in FSHD, experiments were performed to identify which of the four possible genes are the most likely target(s) responsible for DUX4 expression.

FSHD1 myoblasts were transfected with Silencer Select siRNAs (Ambion, Life Technologies) on Day 0. On day 3, samples were harvested for western analysis. On day 4 RNA was harvested for qRT-PCR analysis. RNA samples were done in triplicate and protein samples are singlets. As seen in FIGS. 11A, 11B, 11C, and 12, BRD2 RNA and protein were both selectively depleted with the BRD2 siRNA, BRD3 RNA and protein were selectively depleted using the BRD3 siRNA, and BRD4 RNA and protein were selectively depleted by either of the two BRD4 siRNAs as compared to the various controls.

Figure 13A:
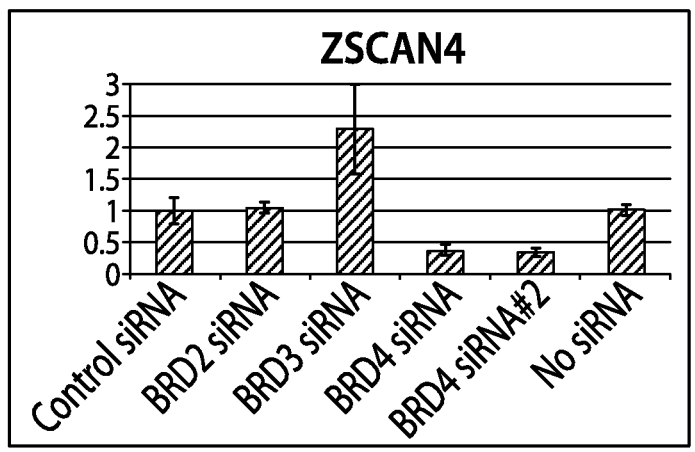
FIGS. 13A, 13B, and 13C shows DUX4 target gene expression after siRNA knockdown. Cells were transfected as above and RNA analyzed 96 h later by qRT-PCR. Error bars indicate standard deviations.
Figure 13B:
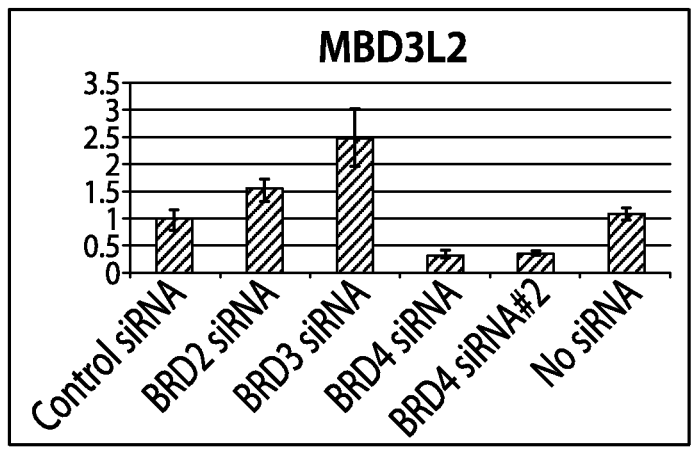
Figure 13C:
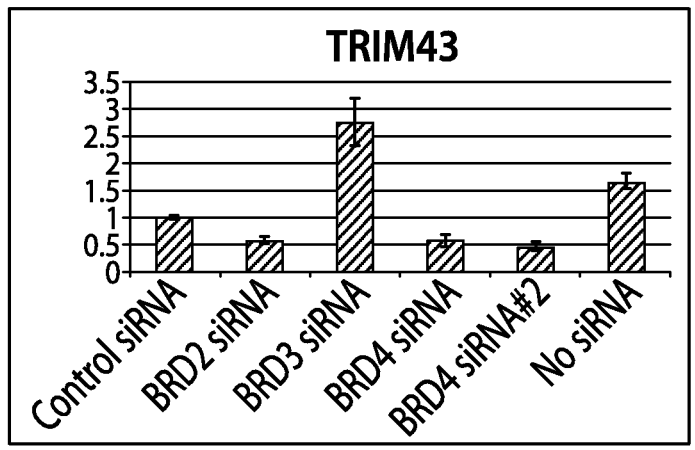
Figure 14A:
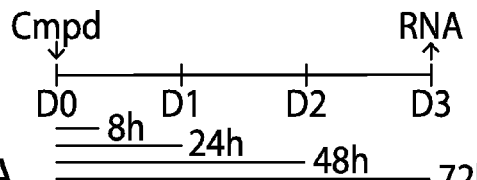
FIGS. 14A, 14B, 14C, 14D, 14E, 14F, and 14G show the exposure-response relationship of DUX4 target and non-target gene expression in FSHD1 myoblasts treated with I-BET762 for various length of time.
Figure 14B:
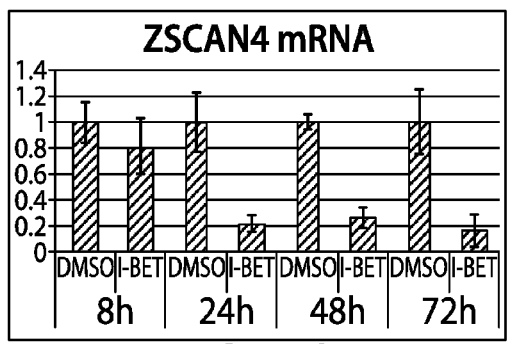
Figure 14C:
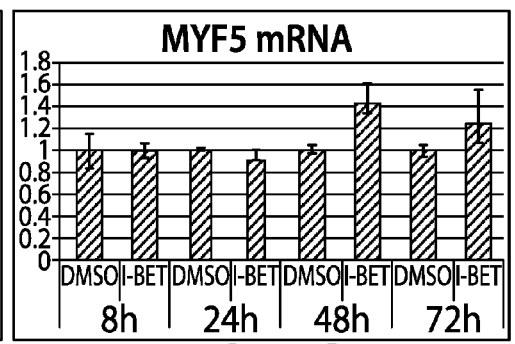
Figure 14D:
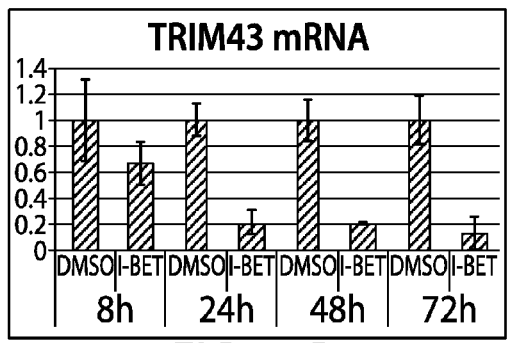
Figure 14E:
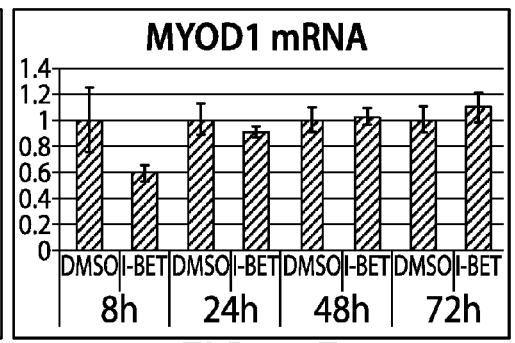
Figure 14F:
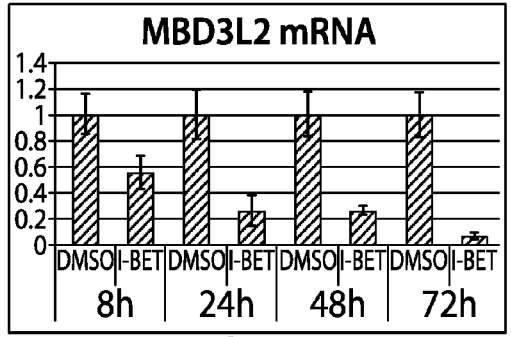
Figure 14G:
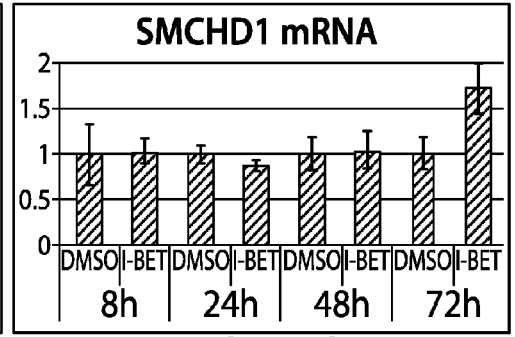

As can be seen in FIGS. 13A, 13B, and 13C, DUX4 targets ZSCAN4, MBD3L2 and TRIM43 were all specifically decreased only with the BRD4 siRNAs (and at a much reduced amount BRD2 siRNAs). These FIGS. indicate that depletion of BRD4, but likely not BRD2 or BRD3, results in decreased DUX4 target gene expression and that BRD4 is the likely target of BET inhibitors that results in BET inhibitor-mediated decreases in DUX4 gene expression. However, the data also indicate that BRD2 or BRD3 inhibition may still provide some benefit. Still further, the fourth BET protein, BRDt, was not reliably detected in FSHD myoblasts due to very low expression and siRNA directed towards BRDt did not affect DUX4 target gene expression (not shown).

This disclosure is currently limited by the availability of highly specific inhibitors for individual gene targets, however, one of ordinary sill in the art would understand that BETi developed in the future that are selective to BRD4 would likely provide highly useful in the treatment of FSHD. While the compounds identified herein here have excellent selectivity profiles for BET bromodomains over all other bromodomains, there are currently few compounds that can selectively inhibit each isoform. However, such a compound would be expected to be useful in the systems and methods discussed herein when discovered.

Continuous exposure of FSHD myoblasts and myotubes in culture to BETi blocked expression of DUX4 and therefore resulted in decreased expression of DUX4 target genes. To determine the exposure-response relationship between BETi and DUX4 expression (pharmacodynamics) in vitro, experiments were performed in both undifferentiated FSHD myoblasts and differentiated FSHD myotubes.

Figure 15A:
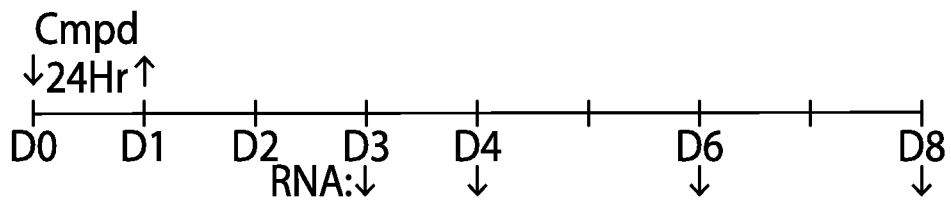
FIGS. 15A, 15B, and 15C show the duration of DUX4 target gene expression response following a 24 hour treatment of FSHD myoblasts with I-BET762.
Figure 15B:
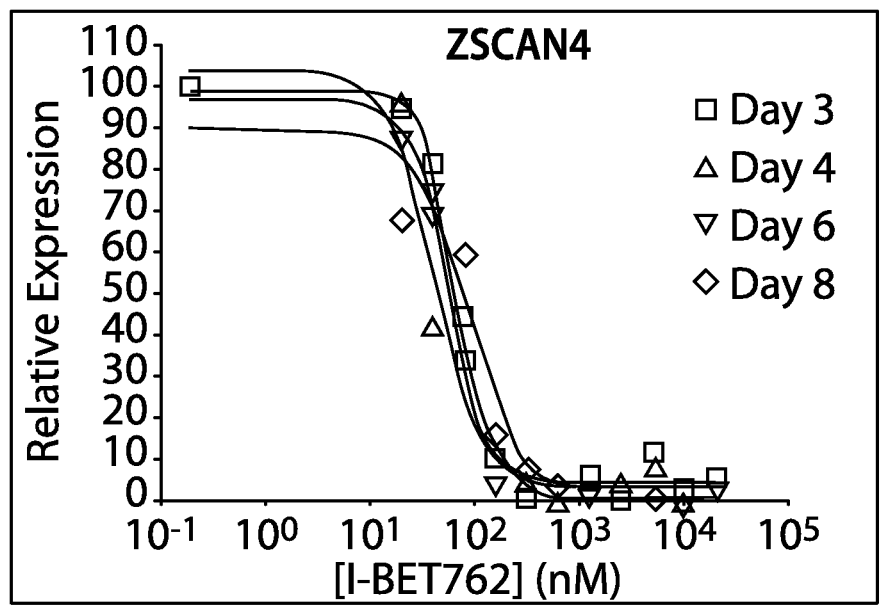
Figure 15C:
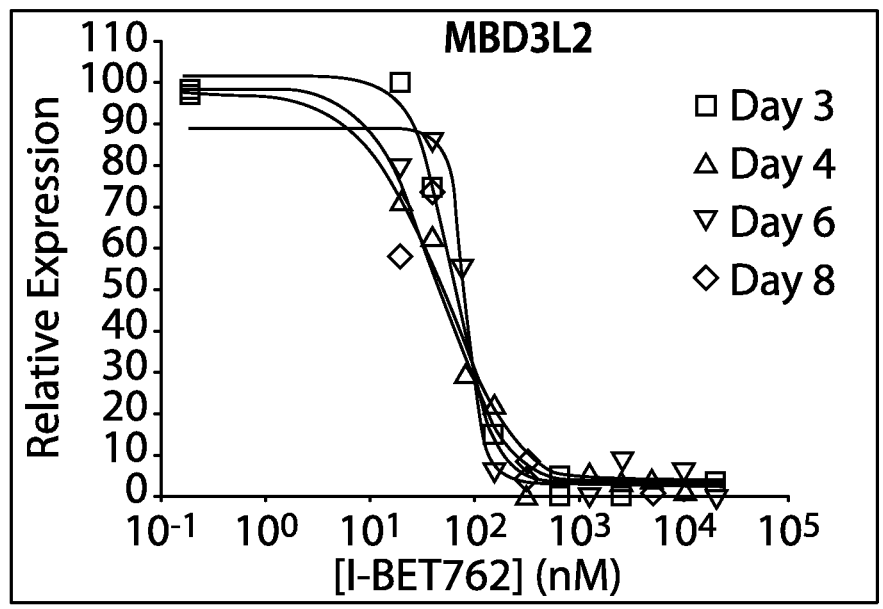

In undifferentiated proliferating FSHD myoblasts, preliminary experiments showed that upon continuous exposure to BETi, decreases in DUX4 target gene expression required 72 h to manifest (not shown). To determine if continuous exposure for the entire 72 h period was required, FSHD1 myoblasts were treated with 500 nM I-BET762 for various lengths of time. At the end of each treatment period, compound was removed, the cells rinsed once and then re-fed with fresh media. At the end of the 72 h time point, RNA was harvested for gene expression analysis. FIGS. 14A-14G show that a 24 hour pulse of BETi was as effective as a full 72 hour exposure in decreasing DUX4 target gene expression (ZSCAN4, TRIM43, MBD3L2). This is surprising in that the drug treatment effect was sustained after removal of compound. Myoblast lineage genes (MYF5, MYOD1) and SMCHD1 (gene that is mutated in FSHD2) were minimally affected by drug treatment. To further explore how long the effects of drug treatment were sustained, FSHD1 myoblasts were treated with a range of I-BET762 concentration for 24 hour before rinsing and re-feeding with fresh media and harvesting at various times up to 8 days after initial treatment. FIGS. 15A-15C demonstrate that the effects of BETi on DUX4 target gene expression are sustained greater than 7 days after removal of drug. This unanticipated result is surprising because BETi have not previously been demonstrated to have long lasting pharmacodynamic effects. Instead, they have been dosed daily in published studies, indicating a requirement for chronic exposure to compounds for sustained effects in animal models. Thus, in an embodiment of the present invention, BETi can be supplied for a pulse window (generally of at least 24 hours although shorter windows may be used) and then withdrawn for a period of time longer than the pulse window. Based on the above, this could be 7 days or more.

Figure 16A:
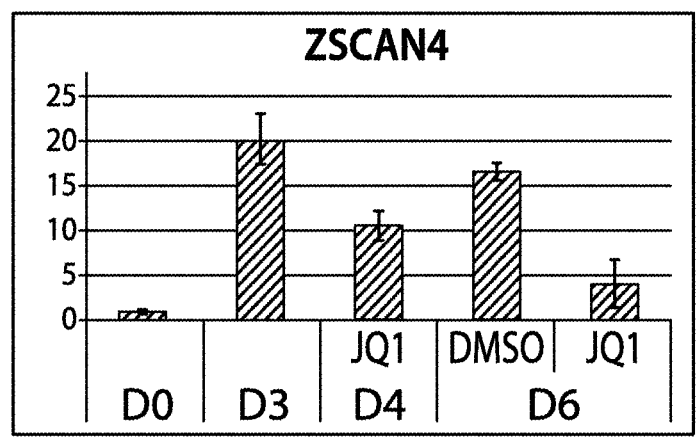
FIGS. 16A and 16B shows a 24 hour exposure of differentiating FSHD myotubes to (+)-JQ1 sustains a decrease in DUX4 target gene expression with minimal effect on differentiation. (+)-JQ1 (500 nM) was added on day 3 (D3) of differentiation and removed on D4. RNA was isolated for qRT-PCR analysis at the indicated time points.
Figure 16B:
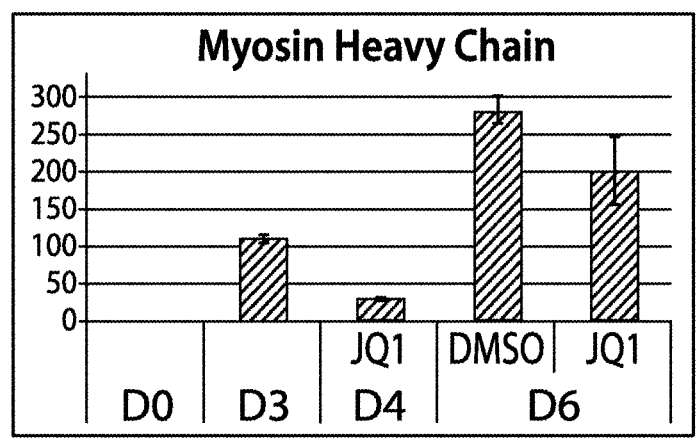

The exposure-response relationship between BETi and DUX4/target gene expression was extended to differentiating FSHD myotubes. FIGS. 16A and 16B demonstrate that a 24 hour pulse of BETi (+)-JQ1 temporarily decreased myosin heavy chain (MYH2, differentiation marker for myotubes) gene expression, but that MYH2 expression rebounded to normal levels when measured 2 days after withdrawal of drug. On the other hand, DUX4 target gene expression (ZSCAN4) continued to decrease 2 days after withdrawing drug. This shows that the pharmacodynamic response of DUX4 is sustained and distinct from that of the differentiation marker MYH2 which is only temporarily decreased. This again highlights the surprising finding that BET inhibition results in sustained decreases in DUX4 gene expression. This may be explained by the infrequent and stochastic nature of DUX4 expression, which is detected in only a fraction of cells in culture at any given time (e.g. 1 in 1,000 cells). The results here suggest that a 24 hour long pulse of BET inhibition disrupts ongoing DUX4 expression that cannot resume after drug withdrawal. New DUX4 expression is presumably governed by the infrequent initiation that occurs due to mutations causing FSHD.

Figure 17A:
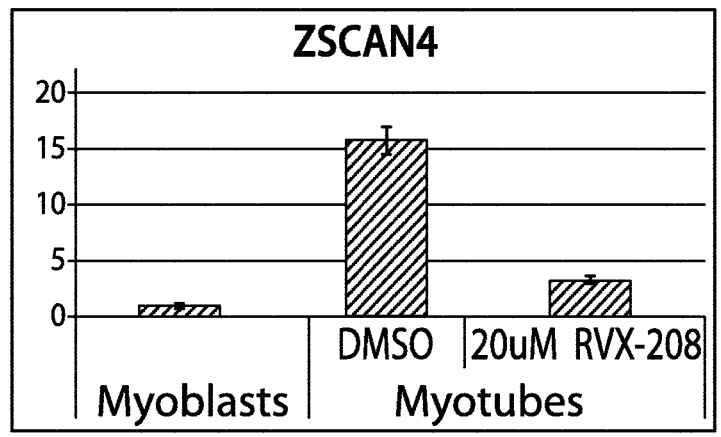
FIGS. 17A and 17B show continuous exposure of FSHD myotubes to RVX-208 during 72 h of differentiation blocks the induction of the DUX4 target ZSCAN4 without affecting the late differentiation marker myosin heavy chain (MHY2).
Figure 17B:
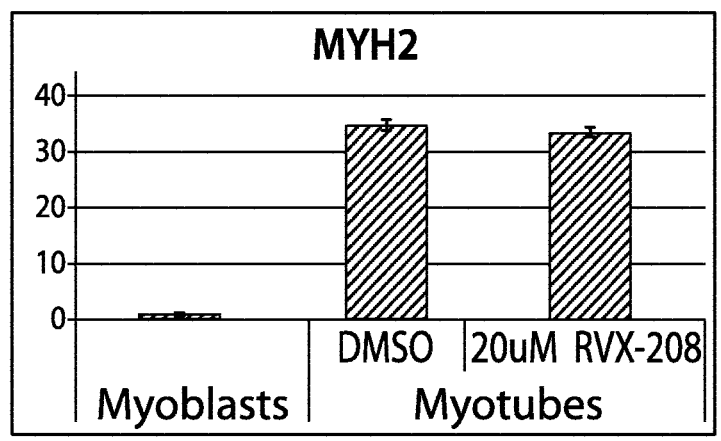

While pulse treatment with most BETi allows recovery of the lineage-specific MYH2 gene expression in myotubes, it is surprising that the BETi RVX-208 did not suppress MYH2 expression upon continuous exposure. FIGS. 17A and 17B demonstrate that 20 µM RVX-208 does not reduce MYH2 expression while significantly reducing DUX4 target gene expression. RVX-208 is different than other known BETi in that it preferentially binds the second of the two bromodomains present in BET proteins (BD2). The functional consequence is that fewer genes are affected by RVX-208. We have shown by two methods (pulse exposure-recovery with inhibitors such as I-BET762 and (+)-JQ1 and continuous exposure to the unique pharmacophore RVX-208) that blocking DUX4 expression via BET inhibition can be achieved without significant unwanted effects on muscle cell differentiation.

While the invention has been disclosed in connection with certain preferred embodiments, this should not be taken as a limitation to all of the provided details. Modifications and variations of the described embodiments may be made without departing from the spirit and scope of the invention, and other embodiments should be understood to be encompassed in the present disclosure as would be understood by those of ordinary skill in the art.

The invention claimed is:
1. A method of reducing muscular weakness from facioscapulohumeral muscular dystrophy (FSHD), the method comprising:

administering to a patient with FSHD a therapeutic quantity of a BET inhibitor (BETi) sufficient to reduce DUX4 expression in said patient.

2. The method of claim 1, wherein said BETi is selected from the group consisting of: (+)-JQ1, PFI-1, I-BET-762, I-BET-151, RVX-208, and CPI-0610.

3. The method of claim 1, wherein said BETi is a selective inhibitor of BRD2.

4. The method of claim 1, wherein said BETi is a selective inhibitor of BRD4.

5. The method of claim 1, wherein said BETi is a broad spectrum inhibitor.

6. The method of claim 1, wherein in said administering said BETi is provided in an initial dose and a second dose is not provided for at least 24 hours after said initial dose.

7. The method of claim 6, wherein said initial dose is provided continuously over 24 hours.

8. The method of claim 6, wherein in said administering, said BETi is provided in an initial dose and a second dose is not provided for at least 48 hours after said initial dose.

9. The method of claim 6, wherein in said administering, said BETi is provided in an initial dose and a second dose is not provided for at least 72 hours after said initial dose.

10. The method of claim 6, wherein in said administering, said BETi is provided in an initial dose and a second dose is not provided for at least 96 hours after said initial dose.

11. The method of claim 1, wherein said patient is human.

* * * * *